United States Patent [19]
Ito et al.

[11] Patent Number: 5,389,531
[45] Date of Patent: Feb. 14, 1995

[54] METHODS TO REPLICATE DNA IN VITRO USING PRD1-CATALYZED DNA REPLICATION SYSTEMS

[75] Inventors: Junetsu Ito, Tucson, Ariz.; Seung-Ku Yoo, Providence, R.I.

[73] Assignee: Arizona Board of Regents, Tucson, Ariz.

[21] Appl. No.: 208,486

[22] Filed: Mar. 9, 1994

Related U.S. Application Data

[63] Continuation of Ser. No. 869,916, Apr. 14, 1992.

[30] Foreign Application Priority Data

Aug. 26, 1991 [JP] Japan ................................ 3-240525

[51] Int. Cl.$^6$ .................... C12Q 1/68; C12P 19/34; C07H 17/00; C12N 15/00
[52] U.S. Cl. ..................................... 435/6; 435/91.1; 435/91.2; 435/172.1; 536/23.1; 536/24.1; 935/1; 935/16; 935/17
[58] Field of Search ............... 435/6, 91.1, 91.2, 172.1; 536/23.1, 24.1; 935/1, 16, 17

[56] References Cited

PUBLICATIONS

Yoo et al., *J. Mol. Biol.*, 218:779–789, 1991, (Apr. 20, 1991).
Savilahti et al., *Gene* 57 (1987) 121–130.
Tamanoi et al. P.N.A.S. 80: 6446–6450 '83.
"Protein–Primed Replication of Bacteriophage PRD1 Genomie in Vitro", by Seung-Ku Yoo and Junetsu Ito, 170 Virology, pp. 442–449 (1989).
"Bacteriophage PRD1 DNA polymerase: Evolution of DNA polymerases", by Guhung Jung, Mark C. Leavitt, Jui–Cheng Hsieh, and Junetsu Ito, 84 Proc. Nat. Acad. Sci., U.S.A., pp. 8287–8291 (1987).
"Primary Structure of the DNA terminal protein of bacteriophage PRD1", by Jui–Cheng Hsieh, Guhung Jung, Mark C. Leavitt, and Junetsu Ito, 15 Nucl. Acids. Res., pp. 8999–9009.
"The complete nucleotide sequence of the left very early region of *Escherichia coli* bacteriophage PRD1 coding for the terminal protein and the DNA polymerase", 57 Gene, pp. 121–130 (1987).
"Molecular Cloning of Bacteriophage PRD1 Genomic Fragments", Mol. Gen. Genet., pp. 233–236 (1983).

*Primary Examiner*—Margaret Parr
*Assistant Examiner*—Bradley L. Sisson
*Attorney, Agent, or Firm*—Cahill, Sutton & Thomas

[57] ABSTRACT

This invention relates to artificial DNAs which are useful in the fields of genetic engineering and medical science and to a method for DNA replication using said DNAs as the replication origin. In one embodiment, this invention provides single- or double-stranded, artificial DNAs having, at the 3' end, a DNA sequence represented by the following general formula:

$$X(Y)_n$$

wherein X denotes the sequence WSSTAWYSS (represented by SEQ ID NO. 1), Y denotes cytidine, guanine, CC or GC, and n is an integer of 1 or 0. In another embodiment, this invention provides a method of DNA replication using PRD1 DNA polymerase and PRD1 terminal protein, which is characterized by the use of single- or double-strand DNAs having the above general formula as the replication origin.

4 Claims, No Drawings

METHODS TO REPLICATE DNA IN VITRO USING PRD1-CATALYZED DNA REPLICATION SYSTEMS

The present invention was made in the course of work conducted under Research Grant NIH-GM28013, from the National Institute of Health, Department of Health and Human Services, United States Public Health Service.

This application is a continuation of application Ser. No. 07/869,916, filed Apr. 14, 1992.

BACKGROUND OF THE INVENTION

This invention relates to artificial DNAs which are useful in the fields of genetic engineering and medical science and to a method for DNA replication using said DNAs as the replication origin.

The replication of a linear DNA duplex unlike that of a circular DNA duplex has an intrinsic problem for completing the 5' ends of the nascent DNA strands. If a DNA polymerase uses short RNA polynucleotides as primers for the initiation of new DNA chain synthesis, removal of the RNA primer from the 5' end of the linear DNA molecule results in an irreparable gap, since all known DNA polymerases synthesize only in a 5' to 3' direction and cannot initiate de novo synthesis of a new chain. This problem was resolved by the discovery of a new DNA polymerase that uses protein as a primer.

The basic features of protein-primed initiation of DNA synthesis are now reasonably clear, and the proteins involved in the replication process have been identified in several systems, although many of the molecular details remain to be elucidated. The first step of the protein-primed DNA replication is the formation of a phosphodiester bond between the $\beta$-hydroxyl group of a specific amino acid residue (serine residue in adenovirus and phage $\phi$29; and tyrosine residue in bacteriophage PRD1) of a terminal protein and the first nucleotide in the new DNA chain (the complex thus formed is hereinafter referred to as the "initiation complex"). This reaction is catalyzed by the viral-encoded DNA polymerase in the presence of PRD1 DNA-terminal protein complex as a template. The nascent strand then grows by extension from the 3'-hydroxyl group of the covalently bound, first nucleotide. Successive elongation by viral DNA polymerase proceeds by concomitant displacement of the 5'-ended strand of the parental DNA. Thus, the 5' ends of the linear DNA can be preserved by the protein-priming mechanism.

Bacteriophage PRD1 is a small, lipid-containing phage, which infects a wide variety of Gram-negative bacteria. The genome of PRD1 is a linear, double-stranded DNA of about 14,700 base pairs ("bp"). A $28 \times 10^3$ Mr terminal protein encoded by PRD1 is covalently linked to the 5' ends of viral genome. The linkage between the terminal protein and PRD1 DNA is a phosphodiester bond between a tyrosine residue of the terminal protein and dGMP, which is the terminal nucleotide for the PRD1 genome. The PRD1 DNA contains perfectly inverted terminal repeats (ITRs) of 110 to 111 base-pairs.

PRD1 DNA replication starts at either one of the DNA ends and proceeds toward the other end. The natural template for in vivo replication of PRD1 DNA is, as in the case of in vitro, the viral chromosome with the terminal protein covalently attached to the 5' end thereof (hereinafter referred to as "PRD1 DNA-terminal protein complex"). The parental terminal protein and ITR are both believed to play important roles in DNA replication as structural parts of the template. The ITRs (or part of them) seem to function as a replication origin. However, the replication mechanism of the bacteriophage PRD1 DNA has not been completely understood, and the region in ITR that acts as the replication origin has not been clarified.

SUMMARY OF THE INVENTION

The objects of this invention are to clarify the replication mechanism of bacteriophage PRD1, particularly the function of ITR, and to provide DNAs useful in the fields of genetic engineering and medical science, and a method of DNA replication using said DNAs, PRD1 DNA polymerase, and PRD1 terminal protein.

In one embodiment, this invention provides single- or double-stranded, artificial DNAs having, at the 3' end, a DNA sequence represented by the following general formula (I):

$$X(Y)_n \qquad (I)$$

(wherein X is the DNA sequence represented by SEQ ID No. 1 of the Sequence Listing; Y denotes cytidine, guanine, CC or GC, and n is an integer of 1 or 0).

In another embodiment, this invention provides a method of DNA replication using PRD1 DNA polymerase and PRD1 terminal protein, which is characterized by the use of the single- or double-strand DNAs of the first embodiment as the replication origin.

The DNAs of this invention are artificial DNAs having at the 3' end a DNA sequence represented by the general formula (I), that is, artificial, single-strand DNAs having, at the 3' end, said DNA sequence; and artificial, double-stranded DNAs containing said DNA sequence at one of the 3' ends or at both of the 3' ends.

An initiation complex is formed at the complementary position of cytidine of the 3' end of DNA of this invention in the presence of PRD1 DNA polymerase and PRD1 terminal protein, thus initiating the DNA replication by PRD1 DNA polymerase and PRD1 terminal protein.

The DNA replication method of this invention may be practiced, for example, by attaching a DNA sequence represented by the above-mentioned general formula (I) to the 3' end of a desired DNA, and performing replication in the presence of PRD1 DNA polymerase, PRD1 terminal protein, ATP, dCTP, dTTP and dATP by the use of the new DNA prepared above as a template. This template DNA may be prepared by a ligation method, a primer extension method, or a DNA synthesis method.

DESCRIPTION OF THE PREFERRED EMBODIMENTS

The genome of bacteriophage PRD1 is a linear, double-stranded DNA of about 14,7000 base-pairs, which is replicated by PRD1 DNA polymerase and PRD1 terminal protein [Virology, 170 442–449 (1989)]. The PRD1 genome DNA contains ITRs on both ends, and the nucleotide sequences of PRD1 DNA polymerase, PRD1 terminal protein, and ITR are known [Proc. Nat. Acad. Sci., U.S.A., 84, 8287–8291 (1987)], [Nucl. Acids. Res., 15 8999–9009 (1987)], [Gene, 57, 121–130 (1987)]. The DNA sequences represented by SEQ ID No. 2 of the Sequence Listing show these 5'-end sequences; Base No. 1–110 are the sequences of left-side ITR (L-ITR), and Base No. 233–1012 and 1016–2677 are sequences of genes coding PRD1 terminal protein and PRD1 DNA polymerase, respectively.

We have determined the generalized DNA sequence for PRD1-initiated DNA replication. The DNA sequence is be represented by the following general formula (I):

$$X(Y)_n \qquad (I)$$

(wherein X is the DNA sequence represented by SEQ ID No. 1 of the Sequence Listing; Y denotes cytidine, guanine, CC or GC, and n is an integer of 1 or 0). SEQ ID No. 1 is the 3' end, and can be correlated with SEQ ID No. 2 in that SEQ ID 1 is the complement to base pairs 2–10 of SEQ ID No. 2.

The replication of PRD1 phage DNA is carried out by recognizing the ITR sequence, but the region of ITR required for DNA replication was not previously known. It was thus necessary to determine this ITR region in order to perform artificial DNA replication.

Determination of this region can be effected by preparing DNAs with various ITR-derived DNAs attached to the ends thereof, and performing DNA replication in the presence of PRD1 DNA polymerase and PRD1 terminal protein.

The present inventors prepared phagemid pEMBL SMA containing ITR. Said phagemid contains L-ITR and genes coding PRD1 terminal protein and PRD1 DNA polymerase, with a sequence cleaved by restriction enzyme SmaI being attached to a site upstream from the L-ITR sequence. *Escherichia coli* NM522 cells transformed by said phagemid were named *Escherichia coli* NM522/pEMBL SMA, which have been deposited at the Fermentation Research Institute, Agency of Industrial Science and Technology, Japan, under FERM BP-3449. The DNA sequences represented by SEQ ID No. 3 of the Sequence Listing are part of the DNA sequences in phagemid pEMBL SMA; Base No. −3—+3 corresponds to the inserted SmaI restriction enzyme site, and Base No. 1–110 is the L-ITR DNA sequence.

DNA having the L-ITR sequence at one end can be easily prepared by digesting said phagemid with SmaI. This SmaI digest exhibits the ability of forming the initiation complex in the presence of PRD1 terminal protein and PRD1 DNA polymerase in vitro, and in vitro DNA replication is initiated even with a linear DNA having no covalent PRD1 terminal protein at the end 5' end.

DNAs with L-ITR, a part of the same, or L-ITR point mutant attached thereto can be easily prepared from the above pEMBL SMA by using the PCR method described by Saiki, et al. [Science, 230 1350–1354 (1985)].

As examples of the DNAs with L-ITR or a part of the same attached thereto, or of the DNAs lacking ITR, may be mentioned those represented by SEQ ID No. 4–11 of the Sequence Listing, and the necessary ITR sequence can be determined by performing DNA replication using the above-described DNAs.

PRD1 DNA polymerase and PRD1 terminal protein used in DNA replication may be prepared by conventional methods [J. Virol, 47, 50, 309–315 (1984)]; for example, may be employed those obtained from *E. coli* HLB3 (pLM2, pLM3) cells containing the genes of PRD1 terminal protein and PRD1 DNA polymerase [Mol. Gen. Genet., 190, 233–236 (1983); Virology, 170, 442–449 (1989)]based on the genetic engineering techniques.

Among the DNAs represented by SEQ ID No. 4–11 of the Sequence Listing, those having, at the 3' end, the DNA represented by SEQ ID no. 12 of the Sequence Listing are replicated through the PRD1 replication mechanism, indicating that the first 10 bp is the important sequence in the ITR sequence.

If DNAs represented by SEQ ID No. 6 of the Sequence Listing, in which the region of Base No. 1–18 is substituted with the sequence represent by SEQ ID No. 13–26, are prepared and their DNA replication activity is measured, the important region for DNA replication in the ITR sequence can be determined. Each of these point mutants has DNA replication activity (template activity), and DNA replication can be performed with DNAs having, at the 3' end, the DNA represented by SEQ ID No. 27 of the Sequence Listing.

The fact that the 3' strand sequence of ITR is the replication origin for the replication by PRD1 DNA polymerase and PRD1 terminal protein can be confirmed, for example, by synthesizing single-stranded DNAs represented by SEQ ID No. 28–30 of the Sequence Listing and measuring the ability of forming the initiation complex; the formation of the initiation complex is confirmed at the complementary site of cytidine of the 3' end of these DNAs.

DNA replication by the use of a DNA of this invention as the replication origin with PRD1 DNA polymerase and PRD1 terminal protein can be effected by attaching, to the 3' end of the DNA to be replicated, a DNA represented by the general formula (I) mentioned above; for example, by attaching, directly or through a linker, a DNA represented by SEQ ID No. 12 or No. 28–47 of the Sequence Listing.

Alternatively, a DNA represented by SEQ ID No. 48–54 or No. 13–26 of the Sequence Listing, having the DNA represented by the general formula (I) at its 3' end, may be attached to a DNA to be replicated directly or through a linker, thus preparing a DNA with a DNA represented by the general formula (I) attached to its 3' end. The attachment may be carried out by the DNA ligation method, by the primer extension method, or by the DNA synthesis method, and a proper method should be selected case by case. Various linkers may also be used for insertion between a DNA of this invention and a DNA to be replicated. These DNAs may be synthesized by a primer with the specific sequence for the DNA to be replicated, or may be synthesized to be used as a double-stranded DNA for replication.

The DNAs of this invention can be employed in the novel DNA replication method using PRD1 DNA polymerase and PRD1 terminal protein, and said DNAs and the novel replication method using the same are useful in various fields using the DNA replication step, such as genetic engineering, genetic diagnosis and the like.

The following Examples will further illustrate the invention but are not intended to limit its scope.

EXAMPLE 1

Preparation of PRD1 DNA Polymerase-PRD1 Terminal Protein Complex Solution

PRD1 DNA polymerase and PRD1 terminal protein were prepared as a complex as described below by using *Escherichia coli* HLB3 (pLM2, pLM3) cells carrying bacteriophage PRD1 gene 1 (DNA polymerase) and gene 8 (terminal protein).

*Escherichia coli* HLB3 (pLM2, pLM3) cells were cultivated at 37° C. in 14-liter of L-broth medium containing 20 μg/ml of tetracycline to approximately $5 \times 10^8$ cells/ml. The cells were collected by centrifugation at 5° C. The cells thus obtained were suspended in 16.8 ml of 5mM TRIS-HCl buffer (pH 7.6) containing 10%(w/v) sucrose and 1 mM dithiothreitol, and egg lysozyme (obtained from Sigma Co. Ltd.) and EDTA were added to the suspension to a final concentration of 300 μg/ml and 1 mM, respectively. The resulting mixture was incubated at 0° C. for 5 minutes, and nonionic detergent Brij58 was then added to it to a final concentration of 0.1%. The resulting mixture was further incubated at 0° C. for 40 minutes, frozen rapidly in a liquid nitrogen bath and then thawed rapidly at 30° C., thus giving lysate. The lysate was adjusted to 0.8M NaCl and centrifuged (200,000 g) at 0°–5° C. for 90 minutes in a Beckman rotor SW50.1. To the supernatant thus obtained, was gradually added ammonium sulfate to 50% saturation, the mixture was stirred for 20 minutes, and the precipitate thus formed was collected by centrifugation. The precipitate thus recovered was dissolved in 8.4 ml of buffer A containing 50 mMTris-HCl (pH 7.6), 1 mM EDTA, and 1 mM dithiothreitol. This solution was passed through a DEAE-cellulose column (1.8×20 cm) equilibrated with buffer A to remove nucleic acids, and the column was eluted with buffer A containing 0.4M NaCl. The flow-through and 0.4M NaCl fractions were mixed together, ammonium sulfate was added to this mixture to 50% saturation, the resulting mixture was stirred for 20 minutes, and the precipitate thus formed was collected by centrifugation. The precipitate thus obtained was suspended in 1 ml of buffer I containing 20 mMTris-HCl (pH 7.0), 20%(v/v) glycerol, 5 mM magnesium chloride, 60 mM ammonium sulfate, and 1 mM β-mercaptoethanol, and the suspension thus obtained was dialyzed overnight against buffer I. The dialyzed cell extract was applied to a phosphocellulose column activated as described by Watabe, et al. [Proc. Natl. Acad. Sci., U.S.A., 81, 5374–5378 (1984)], and the column was eluted with a 400 ml gradient of NaCl (0 to 0.7M) in buffer I. Polymerase activity and complex formation assay were performed to measure replication activity of fractions. PRD1 DNA polymerase PRD1 terminal protein complex was eluted with approximately 0.255M NaCl, and this eluate (hereinafter referred to as "Solution A") was used for in vivo DNA replication experiments.

EXAMPLE 2

Construction of ITR-containing, Phagemid pEMBL SMA, and Measurement for the Template Activity of Said Phagemid Digested with SmaI (1) Construction of Phagemid pEMBL SMA A recombinant plasmid pLM3 is a plasmid containing PRD1 L-ITR and genes coding PRD1 terminal protein and PRD1 DNA polymerase [Mol. Gen. Genet., 190 233–236 (1983)], and hence said plasmid was digested with PstI, thus giving 3 kb DNA fragment containing the above genes and L-ITR.

Separately, phagemid pEMBLex3 [Gene, 37, 199–206 (1985)] was digested with PstI and then dephosphorylated with calf intestinal phosphatase. To the PstI cloning site of the dephosphorylated product thus obtained, was ligated the above-mentioned 3 kb DNA fragment, and this ligation mixture was used for the transformation of *E. coli* NM522 competent cells. Next, screening of the transformants by restriction enzyme and DNA sequence analysis was performed, thus giving recombinant, circular DNA.pEMBL3K (pEMBLex3 with L-ITR and the genes coding PRD1 terminal protein and PRD1 DNA polymerase inserted to the PstI site).

An SmaI-cleaved site was created at the junction of L-ITR and pEMBLex3 in order to linearize pEMBL3K and expose L-ITR at one end because circular DNA does not work as the template for PRD1 DNA polymerase. As the primer for introducing the above SmaI-cleaved site, was used the primer ITR SMA represented by SEQ ID No. 55 of the Sequence Listing, which was synthesized by the use of a Cyclone DNA synthesizer (Milligen/Biosearch) and purified.

Single-stranded pEMBL3K DNA containing uracil was first prepared by the method described by Kunkel, et. al. [Methods Enzymol, 154, 367–382 (1987)]. Said DNA (1 μg) was then incubated together with phosphorylated primer ITR SMA (10 ng), T4 DNA polymerase (1 unit), and T4 DNA ligase (2 to 5 units) at 37° C. for 90 minutes, thus giving a mutated DNA sequence. The resulting double-stranded DNA was used to transform *E. coli* NM522 competent cells. Colonies were selected at random, and screened for the presence of SmaI sites on the phagemid by restriction analysis. Mutation was confirmed by double-stranded DNA sequencing. The phagemid with the SmaI site introduced thereto was named pEMBL SMA, and *E. coli* NM522 cells transformed by said phagemid were named *Escherichia coli* NM522/pEMBL SMA and have been deposited at the Fermentation Research Institute, Agency of Industrial Science and Technology, Japan, under FERM BP-3449. Deletion or site-specific mutagenesis of ITR can be done by the genetic engineering techniques with phagemid pEMBL SMA. DNAs containing a desired DNA sequence and ITR sequence required for replication at a desirable site in the ITR sequence can be simply prepared, and said DNAs can be easily replicated with PRD1 DNA polymerase and PRD1 terminal protein. In addition, said phagemid is useful also for the production of PRD1 DNA polymerase and PRD1 terminal protein.

(2) Measurement of the Template Activity of Phagemid pEMBL SMA Digested with SmaI SmaI-linearized pEMBL SMA containing the full-length L-ITR sequence was tested for the abilty to support protein-primed DNA replication as described below.

Complex formation was performed basically under the same conditions described by Watabe, et al. [Proc. Natl. Acad. Sci., U.S.A., 81, 5374–5378 (1984)].

The standard reaction solution (50 μl) contained 50mM Hepes (pH 7.6), 3 mM dithiothreitol, 5 mM magnesium chloride, 2 mM ATP, 0.5 μM [α-32p] dGTP 93,000 Ci/mmol), DNA to be tested, and 10 μl of solution A described in Example 1. This standard solution was incubated at 25° C. for 30 minutes, and 5 units of RQ1 Dnase (Promega) was then added. The resulting mixture was further incubated at 37° C. for 30 minutes, the reaction was terminated by adding 50 μl of stop solution containing 0.18M sodium pyrophosphate, 0.05 EDTA, and 20% TCA, and incubation was further continued on ice for 5 minutes. After centrifugation, the supernatant was discarded and the precipitate was dissolved in 30 μl of sample buffer containing 0.1M tris-HCl (pH 6.8), 2% SDS, 20% glycerol, 10% β-mercaptoethanol, and 0,005% bromophenol blue. The reaction products were examined on a 12% polyacrylamide- SDS gel by electrophoresis, followed by autoradiogrphy.

When phagemid pEMBL SMA was linearized by SmaI to expose the L-ITR, the terminal protein-free linear DNA was also capable of supporting initiation complex formation like the PRD1 DNA-terminal protein complex. The efficiency was lower than that of the PRD1 DNA-terminal protein complex but was satisfactory with 1 pmol of linear pEMBL SMA (5 μg) under the conditions herein adopted. This result indicates that the terminal protein-free linear, double-stranded DNA containing the ITR sequence at one end can be recognized and replicated by in vivo DNA replication system.

EXAMPLE 3

Preparation of Mutants With Various Deletions and Replication of Said Mutants (1) Synthesis of Primers for Deletion Mutagenesis The following primer DNAs required for deletion mutagenesis were synthesized based on the fact that primers having an add-on sequence at 5' end are introduced into amplifying PCR products.

Primer DEL19-75 represented by SEQ ID No. 56 of the Sequence Listing is the one composed of 5' strand DNA sequences represented by Base No. 1-18 and 76-97 in SEQ ID No. 3 of the Sequence Listing and for obtaining mutants lacking the DNA sequence represented by Base No. 19-75.

Primer DEL21-112 represented by SEQ ID No. 57 of the Sequence Listing is the one composed of 5' strand DNA sequences represented by Base No. 1-20 and 113-132 in SEQ ID No. 3 of the Sequence Listing and for obtaining mutants lacking the DNA sequence represented by Base No. 21-112.

Primer DEL1-113 represented by SEQ ID No. 58 of the Sequence Listing is the one composed of 5' strand DNA sequence represented by Base No. 114-128 in SEQ ID No. 3 of the Sequence Listing and for obtaining mutants lacking the DNA sequence represented by Base No. 1-113.

Primer DEL2-113 represented by SEQ ID No. 59 of the Sequence Listing is the one composed of 5' strand DNA sequences represented by Base No. 1 and No. 114-128 in SEQ ID NO. 3 of the Sequence Listing and form obtaining mutants lacking the DNA sequence represented by Base No. 2-113.

Primer DEL11-113 represented by SEQ ID No. 60 of the Sequence Listing is the one composed of 5' strand DNA sequences represented by Base No. 1-10 and No. 114-123 in SEQ ID No. 3 of the Sequence Listing and for obtaining mutants lacking the DNA sequence represented by Base No. 11-113.

Primer DEL16-113 represented by SEQ ID No. 61 of the Sequence Listing is the one composed of 5' strand DNA sequences represented by Base No. 1-15 and No. 114-125 in SEQ ID No. 3 of the Sequence Listing and for obtaining mutants lacking the DNA sequence represented by Base No. 16-113.

Primer F represented by SEQ ID No. 62 of the Sequence Listing is the one composed of 5' strand sequences represented by Base No. 1-19 in SEQ ID No. 3 of the Sequence Listing and for obtaining products with no deletion.

Reverse primer 1 represented by SEQ ID No. 63 is the one composed of 3' strand DNA sequence represented by Base No. 221-239 in SEQ ID No. 3 of the Sequence Listing which may be used in PCR in combination with each of primers represented By SEQ ID No. 56-62 of the Sequence Listing.

Reverse primer 2 represented by SEQ ID No. 64 is the one composed of 3' strand DNA sequence represented by Base No. 593-607 in SEQ ID No. 3 of the Sequence Listing, which may be used in PCR in combination with primers represented by SEQ ID No. 56-62 of the Sequence Listing.

These primers were synthesized and purified in the same manner as described in Paragraph (1) of Example 2.

(2) DNA amplification by PCR

PCR was carried out in a 100 μl solution containing 1 ng of template DNA (pEMBL SMA), 2.5 units of Tag2T-2DNA polymerase, 100 pmol of each primer, 200 μM each of dATP, dTTP, dGTP and dCTP, 10 mM Tris-HCl (pH 8.3), 50 mM potassium choloride, 1.5 mM magnesium chloride, and 0.01% gelatin. Amplification was performed for 25 cycles with an annealing temperature of 37° C.

PCR was carried out with primer combinations of the following eight types: primer DEL19-75/reverse primer 1, primer DEL21-112/reverse primer 1, primer F/reverse primer 1, primer DEL1-113/reverse primer 2, primer DEL2-113/reverse primer 2, primer DEL1-1-13/reverse primer 2, primer DEL16-113/reverse primer 2, and primer DEL21-112/reverse primer 2.

As strands initiated by these add-on primers were themselves copied, the added terminal sequence became incorporated into the PCR-amplified DNA. The 5' region of the ITR was not amplified except the add-on sequence and hence the amplified product lacked the sequence between the add-on sequence and the hybridization sequence for add-on primers.

PCR using primer DEL19-75 and reverse primer 1 gave 182 bp long double-stranded DNA(A) represented by SEQ ID No. 4 of the Sequence Listing. PCR using primer DEL21-112 and reverse primer 1 gave 147 bp long double-stranded DNA(B) represented by SEQ ID No. 5 of the Sequence Listing. PCR using primer F and reverse primer 1 gave 239 bp long double-stranded DNA(C) represented by SEQ ID No. 6 of the Sequence Listing. Furthermore, PCR using primer DEL1-113 and reverse primer 2 gave 494 bp long double-stranded DNA(D) represented by SEQ ID No. 7 of the Sequence Listing, PCR using primer DEL2-113 and reverse primer 2 gave 495 bp long double stranded DNA(E) represented by SEQ ID No. 8 of the Sequence Listing, PCR using primer DEL11-113 and reverse primer 2 gave 504 bp long double-stranded DNA(F) represented by SEQ ID No. 9 of the Sequence Listing, PCR using primer DEL16-113 and reverse primer 2 gave 509 bp long double-stranded DNA(G) repesented by SEQ ID No. 10 of the Sequence Listing, and PCR using primer DEL21-112 and reverse primer 2 gave 515 bp long double-stranded DNA(H) represented by the SEQ ID No. 11 of the Sequence Listing.

(3) Replication of the Mutants

DNA replication by the PRD1 DNA polymerase-PRD1 terminal protein complex prepared in Example 1 was performed with the DNA lacking a part of the ITR sequence or containing the intact ITR sequence prepared in the above Example as a template.

The standard reaction solution (50 μM) contained 50 mM Tris-HCl (pH 7.6), 10 mM magnesium chloride, 1 mM ATP, 40 μM each of dATP, dGTP, dCTP, and dTTP, 1 μM [$\alpha^{32}$P]dGTP (3,000 Ci/mmol), 1 mM spermidine.3 HCl, 1 mM dithiothreitol, 10%(v/v) glycerol, 1 pmol each of the above-mentioned double-stranded DNA(A)–(H) amplified by PCR, and 10 μl of Solution A prepared in Example 1.

This reaction solution was incubated at 25° C. for 1 hour, treated with proteinase K, and extracted with phenol. The DNA was precipitated with 0.5 volume of 7.5M ammonium acetate and 2.5 volume of 95% ethanol and subjected to electrophoresis on alkaline agarose gel as described below. Alkaline electrophoresis buffer containing 30 mM NaOH and 1 mM EDTA was added to soak into a 1.2% agarose gel prepared in a solution containing 50 mM NaCl and 1 mM EDTA. The above DNAs labeled with $^{32}$P were dissolved in alkaline loading buffer containing 50 mM NaOH, 1 mM EDTA, and 2.5% Ficoll 400, and loaded onto the gel prepared above. After electrophoresis, the gel was immersed in 7% TCA at 25° C. for 30 minutes, and dried for autoradiography. Each band corresponding to full-length DNA was cut out and counted for radioactivity in a liquid scintillation counter. The results thus abtained are shown in Table 1 below, in which the mark "+" indicates that replication of template DNA was effected, and the mark "−" indicates that no such replication was effected.

TABLE 1

| Template DNA | Contained ITR | Replication Activity |
|---|---|---|
| Double-stranded DNA | | |
| (A) | 1–18, 76–110 | + |
| (B) | 1–20 | + |
| (C) | 1–110 | + |
| (D) | None | − |
| (E) | 1 | − |
| (F) | 1–10 | + |
| (G) | 1–15 | + |
| (H) | 1–20 | + |

Analysis of the nucleotide sequence of ITRs (110 to 111 bp long) of PDR1 family members has revealed three distinctive regions. The first 18 bp and the last 35 bp of ITRs are totally conserved in all PRD1 family members examined, and a variable region is present between these conserved nucleotide sequences.

The double-stranded DNA(B) containing only the first 20 bp of the ITR was as good a template as the non-mutated double-stranded DNA (C). This indicates that the rest of the ITR is not necessary for replication. The double-stranded DNA (A) containing all of the conserved regions (1–18 bp and 76–110 bp) but lacking the variable region (19–75 bp) showed about 85% of the replication activity of the non-mutated double-stranded DNA (C).

The double-stranded DNA(D) containing no ITR region and the double-stranded DNA(E) containing only the first nucleotide G did not support replication. Thus, the terminal nucleotide sequence of ITR (10–20 bp) is essential for replication, and the maximum replication activity was shown with the double-stranded DNA containing the terminal 20 bp. These results suggest that the minimal replication origin of PRD1 genome exists within the terminal 20 bp of ITR, and that double-stranded DNAs having, at 3' end, DNA represented by SEQ ID No. 12 and No. 31–33 can be replicated with PRD1 DNA polymerase and PRD1 terminal protein. These double-stranded DNAs are obtained by attaching DNA represented by SEQ ID No. 12 and No. 31–33 of the Sequence Listing to the 3' end of DNAs to be replicated by the ligation method, followed by preparation of the double-stranded DNA with DNA polymerase, by preparing double-stranded DNA represented by SEQ ID No. 48–51 of the Sequence Listing and linking it to the end of DNAs to be replicated, or by the DNA synthesis method.

EXAMPLE 4

Preparation of Mutants with Various Point Mutations, and Replication of Said Mutants The replication origin of PRD1 genome is specifically recognized by DNA replication proteins. In order to investigate the sequence specificity concerned with this recognition, base substitutions were performed in 18 bases at the ITR terminal described in Example 3, and the relationship between the location of point mutations and the replication activity was examined.

(1) Synthesis of Primer for Site-specific Mutagenesis

The fact that the sequences of mutagenic primer are incorporated into PCR-amplified products was also utilized in this case. Each mutagenic primer prepared was the one which was mismatched by one base from the pEMBL SMA target sequence prepared in Example 2.

Primer ITR 1C represented by SEQ ID No. 65 of the Sequence Listing has a DNA sequence of SEQ ID No. 3 in which G is replaced with C in Base No. 1 among Base No. 1–17; primer ITR 2C represented by SEQ ID No. 66 of the Sequence Listing has a DNA sequence of SEQ ID No. 3 in which G is replaced with C in Base No.2 among Base No. 1–17; primer ITR 3C represented by SEQ ID No. 67 of the Sequence Listing has a DNA sequence of SEQ ID No. 3 in which G is replace with C in Base No. 3 among Base No. 1–19; primer ITR 4A represented by SEQ ID No. 68 of the Sequence Listing has a DNA sequence of SEQ ID No. 3 in which G is replaced with A in Base No. 4 among Base No. 9–18; primer ITR 5T represented by SEQ ID No. 69 of the Sequence Listing has a DNA sequence of SEQ ID No. 3 in which A is replaced with T in Base No. 5 among Base No. 9–18; primer ITR 8G represented by SEQ ID No. 70 of the Sequence Listing has a DNA sequence of SEQ ID No. 3 in which C is replaced with G in Base No. 8 among Base No. 6–21; primer ITR 9C represented by SEQ ID No. 71 of the Sequence Listing has a DNA sequence of SEQ ID No. 3 in which G is replaced with C in Base No. 9 among Base No. 6–21; primer ITR 10A represented by SEQ ID No. 72 of the Sequence Listing has a DNA sequence of SEQ ID No. 3 in which T is replaced with A in Base No. 10 among Base No. 6–25; primer ITR 11A represented by SEQ ID No. 73 of the Sequence Listing has a DNA sequence of SEQ ID No. 3 in which G is replaced with A in Base No. 11 among Base No. 6–24; primer ITR 12G represented by SEQ ID No. 74 of the Sequence Listing has a DNA sequence of SEQ ID No. 3 in which C is replaced with G in Base No. 12 among Base No. 6–27; primer ITR 13G represented by SEQ ID No. 75 of the Sequence Listing has a DNA sequence of SEQ ID No. 3 in which C is replaced with G in Base No. 13 among Base No. 6–24; primer ITR 14G represented by SEQ ID No. 76 of the Sequence Listing has a DNA sequence of SEQ ID No. 3 in which C is replaced with G in Base No. 14 among Base No. 6°–25°; primer ITR 15G represented by SEQ ID No. 77 of the Sequence Listing has a DNA sequence of SEQ ID No. 3 in which C is replaced with G in Base No. 15 among Base No. 6–25; and primer ITR 18G represented by SEQ ID No. 78 of the Sequence Listing has a DNA sequence of SEQ ID No. 3 in which C is replaced with G in Base No. 18 among Base No. 6–29.

The primer ITR SMA represented by SEQ ID No. 55 of the Sequence Listing was used for control DNA preparation.

These primers were synthesized and purified in the same manner as in Paragraph (1) of Example 2, and used in PCR.

(2) DNA amplication by PCR

PCR was performed according to the method described in Paragraph (2) of Example 3. Reverse primer 1 described in Paragraph (1) of Example 3 was combined with each of the primers described in Paragraph (1) of Example 4 to form a pair of PCR primers.

PCR by the use of primer ITR 1C and reverse primer 1 produced 239 bp long double-stranded DNA(I) having the DNA sequence represented by SEQ ID No. 13 of the Sequence Listing at its terminal; PCR by the use of primer ITR 2C and reverse primer 1 produced 239 bp long double-stranded DNA(J) having the DNA Sequence represented by SEQ ID No. 14 of the Sequence Listing at its terminal; and PCR by the use of primer ITR 3C and reverse primer 1 produced 239 bp long double-stranded DNA(K) having the DNA sequence represented by SEQ ID No. 15 of the Sequence Listing at its terminal.

PCR by the use of primer ITR 4A and reverse primer 1 amplified DNA having an SmaI restriction site, this DNA was subjected to SmaI digestion, and the 239 bp long fragment thus formed was purified by electrophoresis on polyacrylamide gel, thus giving double-stranded DNA(L) having the DNA represented by SEQ ID No. 16 of the Sequence Listing at its terminal.

PCR by the use of primer ITR 5T and reverse primer 1 amplified DNA having an SmaI restriction site, this DNA was subjected to SmaI digestion, and the 239 bp long fragment thus formed was purifed by electrophoresis on polyacrylamide gel, thus giving double-stranded DNA(M) having the DNA represented by SEQ ID No. 17 of the Sequence Listing at its terminal.

PCR by the use of primer ITR 8G and reverse primer 1 amplified DNA having an SmaI restriction site this DNA was subjected to SmaI digestion, and the 239 bp long fragment thus formed was purifed by electrophoresis on polyacrylamide gel, thus giving double-stranded DNA(N) having the DNA represented by SEQ ID No. 18 of the Sequence Listing at its terminal.

PCR by the use of primer ITR 9C and reverse primer 1 amplified DNA having an SmaI restriction site, this DNA was subjected to SmaI digestion, and the 239 bp long fragment thus formed was purifed by electrophoresis on polyacrylamide gel, thus giving double-stranded DNA(O) having the DNA represented by SEQ ID No. 19 of the Sequence Listing at its terminal.

PCR by the use of primer ITR 10A and reverse primer 1 amplified DNA having an SmaI restriction site, this DNA was subjected to SmaI digestion, and the 239 bp long fragment thus formed was purifed by electrophoresis on polyacrylamide gel, thus giving double-stranded DNA(P) having the DNA represented by SEQ ID No. 20 of the Sequence Listing at its terminal.

PCR by the use of primer ITR 11A and reverse primer 1 amplified DNA having an SmaI restriction site, this DNA was subjected to SmaI digestion, and the 239 bp long fragment thus formed was purifed by electrophoresis on polyacrylamide gel, thus giving double-stranded DNA(Q) having the DNA represented by SEQ ID No. 21 of the Sequence Listing at its terminal.

PCR by the use of primer ITR 12G and reverse primer 1 amplified DNA having an SmaI restriction site, this DNA was subjected to SmaI digestion, and the 239 bp long fragment thus formed was purifed by electrophoresis on polyacrylamide gel, thus giving double-stranded DNA(R) having the DNA represented by SEQ ID No. 22 of the Sequence Listing at its terminal.

PCR by the use of primer ITR 13G and reverse primer 1 amplified DNA having an SmaI restriction site, this DNA was subjected to SmaI digestion, and the 239 bp long fragment thus formed was purifed by electrophoresis on polyacrylamide gel, thus giving double-stranded DNA(S) having the DNA represented by SEQ ID No. 23 of the Sequence Listing at its terminal.

PCR by the use of primer ITR 14G and reverse primer 1 amplified DNA having an SmaI restriction site, this DNA was subjected to SmaI digestion, and the 239 bp long fragment thus formed was purifed by electrophoresis on polyacrylamide gel, thus giving double-stranded DNA(T) having the DNA represented by SEQ ID No. 24 of the Sequence Listing at its terminal.

PCR by the use of primer ITR 15G and reverse primer 1 amplified DNA having an SmaI restriction site, this DNA was subjected to SmaI digestion, and the 239 bp long fragment thus formed was purified by electrophoresis on polyacrylamide gel, thus giving double-stranded DNA(U) having the DNA represented by SEQ ID No. 25 of the Sequence Listing at its terminal.

PCR by the use of primer ITR 18G and reverse primer 1 amplified DNA having an SmaI restriction site, this DNA was subjected to SmaI digestion, and the 239 bp long fragment thus formed was purifed by electrophoresis on polyacrylamide gel, thus giving double-stranded DNA(V) having the DNA represented by SEQ ID No. 26 of the Sequence Listing at its terminal.

PCR by the use of primer ITR SMA and reverse primer 1 amplified DNA having a SmaI restriction site, this DNA was subjected to SmaI digestion, and the 239 bp long fragment thus formed was purifed by electrophoresis on polyacrylamide gel, thus giving double-stranded DNA($C^1$) having the same sequence as that of double-stranded DNA(C) described above.

(3) Replication of the Mutants

DNA replication by the PRD1 DNA polymerase-PRD1 terminal protein complex prepared in Example 1 was performed with the double-stranded DNA(I)–(V) or the control double-stranded DNA($C^1$) prepared in the above Example as a template. The reaction conditions and assay conditions were as described in Paragraph (3) of Example 3. The results obtained are shown in Table 2 below, in which the mark "++++" indicates 81–100% replication activity, the mark "+++" indicates 61–80% replication activity, the mark "++" indicates 41–60% replication activity, and the mark "+" indicates replication activity of 40% or less.

TABLE 2

| Template DNA | Replication Activity |
| --- | --- |
| Double-stranded DNA | |
| (I) | ++ |
| (J) | ++ |
| (K) | +++ |
| (L) | + |
| (M) | + |
| (N) | ++++ |
| (O) | +++ |
| (P) | +++ |
| (Q) | + |
| (R) | ++++ |
| (S) | ++ |

TABLE 2-continued

| Template DNA | Replication Activity |
|---|---|
| (T) | + |
| (U) | ++ |
| (V) | + |
| (C¹) | ++++ |

Among the twenty bases of ITR represented by SEQ ID No. 33 of the Sequence Listing, the five bases at 5' end (GGGGA) and the five bases at 3' end (TCCCC), or the four bases starting from G which is the sixth base from 5' end (GGGG) and the four bases at 3' end (CCCC), are complementary with each other. When point mutation was introduced to nucleotides in these complementary regions, a significant decrease in replication activity was observed in eight among ten point mutants, but little change in replication activity was observed in three among four mutants when point mutation was introduced to nucleotides in non-complementary regions. These results indicate the importance of these complementary sequences for protein-primed replication. However, although the decline in replication activity was observed in all of the mutated DNAs, there was no case in which the activity was completely lost. Thus, double-stranded DNAs having, at 3' end, DNA represented by SEQ ID NO. 34–47 can be replicated with PRD1 DNA polymerase and PRD1 terminal protein. These double-stranded DNAs can be obtained by attaching DNA represented by SEQ ID No. 34–47 of the Sequence Listing to 3' end of DNAs to be replicated by the ligation method, followed by preparation of the double-stranded DNA with DNA polymerase by preparing double-stranded DNA represented by SEQ ID No. 13–26 and attaching it to the end of DNAs to be replicated, or by the DNA synthesis method.

EXAMPLE 5

Preparation of ITR 3' strand DNA, and Measurement of the Template Activity (1) Preparation of ITR 3' strand DNA In order to determine the nucleotide sequence at 3' end required for DNA replication, DNAs represented by SEQ ID No. 28–30 and No. 79–85 of the Sequence Listing were prepared and purified in a similar manner as in Paragraph (1) of Example 2.

The DNA represented by SEQ ID No. 28 of the Sequence Listing is made up of the 3' strand DNA sequence represented by Base No. 1-27 in SEQ ID No. 3 of the Sequence Listing; the DNA represented by SEQ ID No. 29 of the Sequence Listing is made up of the 3' strand DNA sequence represented by Base No. 2-27 in SEQ ID No. 3 of the Sequence Listing; the DNA represented by SEQ ID No. 30 of the Sequence Listing is a DNA sequence prepared by attaching C to 3' end of the DNA represented by SEQ ID No. 28; the DNA represented by SEQ ID No. 79 of the Sequence Listing is polyA (27mers), the DNA represented by SEQ ID No. 80 of the Sequence Listing is PolyC (27mers); the DNA represented by SEQ ID No. 81 of the Sequence Listing is PolyG (27mers); the DNA represented by SEQ ID No. 82 of the Sequence Listing is made up of the 3' strand DNA sequence represented by Base No. 3-27 in SEQ ID No. 3 of the Sequence Listing; the DNA represented by SEQ ID No. 83 of the Sequence Listing is made up of the 3' strand DNA sequence represented by Base No. 4-27 of the Sequence Listing; the DNA represented by SEQ ID No. 84 of the Sequence Listing is made up of the 3' strand DNA sequence represented by Base No. 5-27 in SEQ ID No. 3 of the Sequence Listing; and the DNA represented by SEQ ID No. 85 of the Sequence Listing is made up of the 3' strand DNA sequence represented by Base No. 12-27 in SEQ ID No. 3 of the Sequence Listing.

(2) Measurement of the template activity

The template activity was measured by using the DNAs described above according to the method described in Paragraph (2) of Example 2.

Increasing amounts of the DNA represented by SEQ ID No. 28 of the Sequence Listing were added to the standard reaction solution and the reaction products were examined by autoradiography. As a result, the DNA represented by SEQ ID No. 28 of the Sequence Listing was found to form the initiation complex when used in an amount of 100 pmol or higher, indicating that the 3' strand of PRD1 DNA is a template for protein-primed DNA replication, and that the replication origin is the terminal 20 bases of PRD1 DNA genome. On a molar basis, the template efficiency of the synthetic oligonucleotide was about 100 times lower than that obtained with phagemid (pEMBL SMA linearized with SmaI) but addition of 1000 pmol of oligonucleotide resulted in significant transfer of dGMP onto the terminal protein.

In order to determine the necessary sequence of the 3' terminal bases and the initiation site for protein-priming, DNAs represented by SEQ ID No. 29, 30 and 79-85 of the Sequence Listing (1 nmol each) were subjected to reaction under standard conditions, wherein DNAs represented by SEQ ID No. 79-81 of the Sequence Listing were used as negative control. The template activity was completely lost when two or more bases were eliminated from the 3' end of ITR; and DNA lacking the first C residue at the 3' end showed a lower level of the template activity (35%). These results indicate that the initiation of in vivo replication of PRD1 DNA requires a specific DNA sequence at the 3' end even in the case of a single-stranded template, and that replication starts from the first C residue of the 3' end.

The template acitivty of the DNA represented by SEQ ID No. 30 of the Sequence Listing, in which one C residue is further added on the 3' side of the 20 bases of the 3' end, was about 70%, compared with that of the DNA represented by SEQ ID No. 28 of the Sequence Listing.

In the DNA replication with PRD1 DNA polymerase and PRD1 terminal protein, the replication origin is strand specific and the specific DNA sequence of this invention is required for the initiation of DNA replication even in the case of a single-stranded template.

DNA represented by SEQ ID No. 28-30, attached to the 3' end of DNAs, works as the origin in DNA replication with PRD1 DNA polymerase and PRD1 terminal protein, and DNAs having, at the end, DNA represented by SEQ ID No. 52-54, can be replicated by PRD1 DNA polymerase and PRD1 terminal protein.

This invention provides DNAs which are useful as replication origin, and also provides a novel replication method for desired DNAs, which are widely applicable in the fields concerned with DNA, such as genetic engineering and medical science.

SEQUENCE LISTING ( 1 ) GENERAL INFORMATION:

( i i i ) NUMBER OF SEQUENCES: 89

( 2 ) INFORMATION FOR SEQ ID NO: 1:

( i ) SEQUENCE CHARACTERISTICS:
        ( A ) LENGTH: 9 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO: 1:

W S S T A W Y S S         9

( 2 ) INFORMATION FOR SEQ ID NO: 2:

( i ) SEQUENCE CHARACTERISTICS:
        ( A ) LENGTH: 2974 base pairs
        ( B ) TYPE: nucleic acid
        ( C ) STRANDEDNESS: Double
        ( D ) TOPOLOGY: Linear ( i i ) MOLECULE TYPE: Genomic DNA ( i x ) FEATURES: 1-110 E CDS (L-ITR)
                        233-1012 E CDS (PRD1 terminal protein)
                        1016-2677 E CDS (PRD1 DNA polymerase)

( x i ) SEQUENCE DESCRIPTION: SEQ ID NO: 2:

```
GGGGATACGT  GCCCCTCCCC  ACCTACCCGC  GCCCCTAACA  TTTTTATTTC  CGTCTGTCAA    60
TACCCCCTGC  ATCCGATAGG  CCCGAACTAT  CACAAACGGA  AAAGCGATAG  CCCAAAACAC   120
TAAGCCCCTT  TTCATCATTT  CATTTGTAAG  CGCGTTTAAA  ATCATGGTAA  AATAACCACT   180
ACCCCAAATT  GCGCCCCTGC  AATTTGCTGA  CGGTTTAACG  GAAGGCGGAA  ACATGGCGAA   240
GAAAAAACCA  GTAGAAAAAA  ATGGGCTTGT  TTATAAAGAG  TTTCAAAAAC  AAGTTTCAAA   300
TTTGAAGAAA  GCCGGACTAA  TCCCTAAAAC  CCTTGACGTG  CGAAAAGTCA  AGCCAACAAA   360
ACACTATAAA  GGATTGGTAA  GCAAATATAA  AGACGTTGCA  ACAGGGGCG   CTAAACTTGC   420
AGCAATCCCT  AACCCCGCCG  TTATTGAAAC  GCTTGAAGCG  CGGGGCGAAT  CCATCATTAA   480
GAAAGGCGGC  AAGGCGTATC  TGAAAGCCCG  CCAGCAAATA  AACCAGCGCG  GGCAAATTGT   540
AAACCCCTTT  ACGGTTCGCG  TAACCAAACG  CGGCGAAGTG  GTGCGCCGCT  ACCGCAAGAC   600
TACCCCGGAA  GGCAAGCCCG  TTTATATCAC  GCAACGGGAA  TTGCCTATTA  AGTTTGAAAA   660
TATGGAACAG  TGGCTTACTG  AATTAAAGGC  CGCTGGTTTT  CAATTGCAAC  CGGGCGAACA   720
AATCTATTTC  ACTTTTAACG  GCAACTATTC  CCGCCGTACC  TATACGTCAT  TGATGAAGC    780
GTTCAATAAA  TTTATGACGT  ATGACATTAT  TATTGATGCG  GTGGCCGGAA  AATTAAAAGT   840
AGAAGATGAA  GCCGATTTAG  TTAAGTCGGT  AGGCTTTCAA  CGTATCAGCG  GCCCCGAAGC   900
CAAGGCGTAT  AACCGTAACC  GTATTGTATT  GCCTGAAATG  CAATTTAGCC  AAGCGGCTAA   960
AAAGAAATAC  AAGCGCCGTC  AAAAACGCGG  CTATGGCAGC  AAGGGGGTTT  AAGATATGCC  1020
GCGCCGTTCC  CGTAAAAAGG  TGGAATATAA  AATTGCCGCC  TTTGACTTTG  AAACTGACCC  1080
TTTCAAGCAT  GACCGAATCC  CTAAACCGTT  TTCATGGGGT  TTTTATAATG  GCGAAATTTA  1140
TAAAGACTAT  TGGGGCGATG  ATTGCATAGA  ACAGTTTATT  TACTGGCTGG  ATACCATAGA  1200
AGAACCGCAC  GTTATATACG  CTCATAACGG  CGGCAAGTTT  GATTTTCTTT  TTCTCATGAA  1260
ATACTTTCGC  GGGAAATTGA  AAATAGTTAA  TGGGCGTATT  TTGGAAGTAG  AACACGGCAT  1320
CCATAAATTC  CGCGATAGTT  ATGCAATCCT  GCCGGTGCCG  CTTGCTGCCA  GCGATGAAAA  1380
GATAGAAATT  GATTATGGCA  AGATGGAAAG  GGAAACACGC  GAACAGCACA  AGGCGGAAAT  1440
TTTAGAATAC  CTGAAAGGCG  ATTGTGTAAC  CCTGCATAAA  ATGGTTTCTT  TATTTATTGC  1500
TGAATTTGGA  ATGCGCCTAA  CCATAGGCGG  TACGGCAATG  AATGAATTAA  AACAGTTCCA  1560
CCCTTATGAC  CCTGTGCGCA  AAGGCTTTGA  TGAAGCCATG  CGCCCCTTTT  ATTTGGCGG   1620
AAGGTGCCAA  GCATTCGAGA  AAGGAATAAT  TGAAGATGAT  ATAAAGTTT   ATGATGTTAA  1680
TAGTATGTAC  CCCCATGCTA  TGCGAAATTT  CCGCCATCCT  TTCAGCGATG  AATTTTATGA  1740
AGCCAATGAA  ATAACAGAAG  AAACTTATTT  TATTGAATGG  GAAGGCGAGA  ATAACGGCGC  1800
GGTGCCTGTT  AGGACTAAAA  CAGGTTTAGA  CTTTAATCAG  CGTAGCGGCA  TTTTCCATAC  1860
GTCAATCCAT  GAATGGCGGG  CGGGTATTGA  TACCGGCACG  ATTAAACCTA  ATCGGATTAT  1920
AAGGACAATC  AATTTTACTG  AAACAACCAC  TTCGGCGCA   TTCATTGACC  ATTTCTTTAG  1980
CAAGCGTGAC  GCTGCCAAAA  AGGCGGGTGA  TTTATTCCAC  AATATTTTTT  ATAAACTGAT  2040
TTTAAATAGC  AGTTATGGGA  AGTTTGCACA  AAACCCCGAA  AATTATAAAG  AGTGGTGCAT  2100
AACGGAAGGC  GGCATTTATT  TAGAAGGCTA  TGACGGCGAA  GGGTGCGAAG  TACAGGAACA  2160
TTTAGACTAT  ATTTTATGGG  GTAGGCCCGC  TGAAATGTTT  AATTATTTTA  ACGTGGCAGT  2220
GGCGGCAAGT  ATTACAGGCG  CGGCCCGTTC  CGTTTTATTG  CGGGCATTGG  CGCAAGCGGA  2280
AAGGCCGCTT  TATTGTGACA  CTGATTCTAT  TATTTGCCGT  GATTTAAAAA  ATGTTCCGCT  2340
TGACGCTTAC  CAGCTAGGCG  CGTGGGATTT  GGAAGCAACC  GGCGATAAAA  TAGCGATTGC  2400
CGGTAAAAAA  TTATATGCGC  TTTACGCTGG  TGATAATTGC  GTTAAAATTG  CAAGTAAGGG  2460
GGCTAGTCTG  GTTCCGCGTG  ATATTGGGTT  TTTAATGCCC  CCGGATATGG  AACCGAAAGC  2520
CGCCAAAAAG  GTAGCGCAAC  AAAAGGCTAA  AAATATTGGT  GGCGAGAAAA  TTTTAAAGGT  2580
GGCTAATGGC  GGCGTGTATG  ATTTTGTAAA  TGATGCCCCG  TCATTTAAGC  TAAATGGCAA  2640
CGTGCAATTT  ATCAAGCGCA  CAATCAAAGG  AACATAAAAT  GCAATATACA  CTTTGGGATA  2700
TTATCAGCCG  CGTGGAAAGC  AACGGGAATT  TAAAGCGTT   GCGCTTTGAA  CCTGAATACT  2760
ATCAGCGGCG  CATGGAGCGG  GGCGATTGGG  ATAATTCCAT  TATTCAAAAT  ATCCGCGCCG  2820
```

```
CCAATAAATG CAGCTTAGGT ACTGCCCGCA TGATTTATTG CAGTTCATGG GGCGCGGTTC  2880
AAATCATGGG ATTTAATCTT TATTTGAACG GCGCATTTAA TTTGAGCGTT GCGCATTTCA  2940
TGGAAAATGA AGCGTATCAA GTAAATGAAT TTCG                              2974
```

(2) INFORMATION FOR SEQ ID NO:3:

(i) SEQUENCE CHARACTERISTICS:
        (A) LENGTH: 737 base pairs
        (B) TYPE: Nucleic acid
        (C) STRANDEDNESS: Double
        (D) TOPOLOGY: Linear (ii) MOLECULE TYPE: Genomic DNA (ix) FEATURE: 1-110 E CDS (L-ITR)

(xi) SEQUENCE DESCRIPTION: SEQ ID NO: 3:

```
                                        GTCGACC    TGCAGGGCCC   17
GGGGATACGT GCCCCTCCCC ACCTACCCGC GCCCCTAACA TTTTTATTTC CGTCTGTCAA  77
TACCCCCTGC ATCCGATAGG CCCGAACTAT CACAAACGGA AAAGCGATAG CCCAAAACAC 137
TAAGCCCCTT TTCATCATTT CATTTGTAAG CGCGTTTAAA ATCATGGTAA AATAACCACT 197
ACCCCAAATT GCGCCCCTGC AATTTGCTGA CGGTTTAACG GAAGGCGGAA ACATGGCGAA 257
GAAAAAACCA GTAGAAAAAA ATGGGCTTGT TTATAAAGAG TTTCAAAAAC AAGTTTCAAA 317
TTTGAAGAAA GCCGGACTAA TCCCTAAAAC CCTTGACGTG CGAAAAGTCA AGCCAACAAA 377
ACACTATAAA GGATTGGTAA GCAAATATAA AGACGTTGCA ACAGGGGGCG CTAAACTTGC 437
AGCAATCCCT AACCCCGCCG TTATTGAAAC GCTTGAAGCG CGGGGCGAAT CCATCATTAA 497
GAAAGGCGGC AAGGCGTATC TGAAAGCCCG CCAGCAAATA AACCAGCGCG GGCAAATTGT 557
AAACCCCTTT ACGGTTCGCG TAACCAAACG CGGCGAAGTG GTGCGCCGCT ACCGCAAGAC 617
TACCCCGGAA GGCAAGCCCG TTTATATCAC GCAACGGGAA TTGCCTATTA AGTTTGAAAA 677
TATGGAACAG TGGCTTACTG AATTAAAGGC CGCTGGTTTT CAATTGCAAC CGGGCGAACA 737
```

(2) INFORMATION FOR SEQ ID NO: 4:

(i) SEQUENCE CHARACTERISTICS:
        (A) LENGTH: 182 base pairs
        (B) TYPE: nucleic acid
        (C) STRANDEDNESS: double
        (D) TOPOLOGY: linear (xi) SEQUENCE DESCRIPTION: SEQ ID NO: 4:

```
GGGGATACGT GCCCCTCCAT AGGCCCGAAC TATCACAAAC GGAAAAGCGA TAGCCCAAAA  60
CACTAAGCCC CTTTTCATCA TTTCATTTGT AAGCGCGTTT AAAATCATGG TAAAATAACC 120
ACTACCCCAA ATTGCGCCCC TGCAATTTGC TGACGGTTTA ACGGAAGGCG AAACATGGC  180
GA                                                                182
```

(2) INFORMATION FOR SEQ ID NO: 5:

(i) SEQUENCE CHARACTERISTICS:
        (A) LENGTH: 147 base pairs
        (B) TYPE: nucleic acid
        (C) STRANDEDNESS: double
        (D) TOPOLOGY: linear (xi) SEQUENCE DESCRIPTION: SEQ ID NO: 5:

```
GGGGATACGT GCCCCTCCCC CAAAACACTA AGCCCCTTTT CATCATTTCA TTTGTAAGCG  60
CGTTTAAAAT CATGGTAAAA TAACCACTAC CCCAAATTGC GCCCCTGCAA TTTGCTGACG 120
GTTTAACGGA AGGCGGAAAC ATGGCGA                                     147
```

(2) INFORMATION FOR SEQ ID NO: 6:

(i) SEQUENCE CHARACTERISTICS:
        (A) LENGTH: 239 base pairs
        (B) TYPE: nucleic acid
        (C) STRANDEDNESS: double
        (D) TOPOLOGY: linear (xi) SEQUENCE DESCRIPTION: SEQ ID NO: 6:

```
GGGGATACGT GCCCCTCCCC ACCTACCCGC GCCCCTAACA TTTTTATTTC CGTCTGTCAA  60
TACCCCCTGC ATCCGATAGG CCCGAACTAT CACAAACGGA AAAGCGATAG CCCAAAACAC 120
TAAGCCCCTT TTCATCATTT CATTTGTAAG CGCGTTTAAA ATCATGGTAA AATAACCACT 180
ACCCCAAATT GCGCCCCTGC AATTTGCTGA CGGTTTAACG GAAGGCGGAA ACATGGCGA  239
```

(2) INFORMATION FOR SEQ ID NO: 7:

( i ) SEQUENCE CHARACTERISTICS:
   ( A ) LENGTH: 494 base pairs
   ( B ) TYPE: nucleic acid
   ( C ) STRANDEDNESS: double
   ( D ) TOPOLOGY: linear ( x i ) SEQUENCE DESCRIPTION: SEQ ID NO: 7:

| | | | | | | |
|---|---|---|---|---|---|---|
| AAAACACTAA | GCCCCTTTTC | ATCATTTCAT | TTGTAAGCGC | GTTTAAAATC | ATGGTAAAAT | 60 |
| AACCACTACC | CCAAATTGCG | CCCCTGCAAT | TTGCTGACGG | TTTAACGGAA | GGCGGAAACA | 120 |
| TGGCGAAGAA | AAAACCAGTA | GAAAAAAATG | GGCTTGTTTA | TAAAGAGTTT | CAAAAACAAG | 180 |
| TTTCAAATTT | GAAGAAAGCC | GGACTAATCC | CTAAAACCCT | TGACGTGCGA | AAAGTCAAGC | 240 |
| CAACAAAACA | CTATAAAGGA | TTGGTAAGCA | AATATAAAGA | CGTTGCAACA | GGGGGCGCTA | 300 |
| AACTTGCAGC | AATCCCTAAC | CCCGCCGTTA | TTGAAACGCT | TGAAGCGCGG | GGCGAATCCA | 360 |
| TCATTAAGAA | AGGCGGCAAG | GCGTATCTGA | AAGCCCGCCA | GCAAATAAAC | CAGCGCGGGC | 420 |
| AAATTGTAAA | CCCCTTTACG | GTTCGCGTAA | CCAAACGCGG | CGAAGTGGTG | CGCCGCTACC | 480 |
| GCAAGACTAC | CCCG | | | | | 494 |

( 2 ) INFORMATION FOR SEQ ID NO: 8:

( i ) SEQUENCE CHARACTERISTICS:
   ( A ) LENGTH: 495 base pairs
   ( B ) TYPE: nucleic acid
   ( C ) STRANDEDNESS: double
   ( D ) TOPOLOGY: linear ( x i ) SEQUENCE DESCRIPTION: SEQ ID NO: 8:

| | | | | | | |
|---|---|---|---|---|---|---|
| GAAAACACTA | AGCCCCTTTT | CATCATTTCA | TTTGTAAGCG | CGTTTAAAAT | CATGGTAAAA | 60 |
| TAACCACTAC | CCCAAATTGC | GCCCCTGCAA | TTTGCTGACG | GTTTAACGGA | AGGCGGAAAC | 120 |
| ATGGCGAAGA | AAAAACCAGT | AGAAAAAAAT | GGGCTTGTTT | ATAAAGAGTT | TCAAAAACAA | 180 |
| GTTTCAAATT | TGAAGAAAGC | CGGACTAATC | CCTAAAACCC | TTGACGTGCG | AAAAGTCAAG | 240 |
| CCAACAAAAC | ACTATAAAGG | ATTGGTAAGC | AAATATAAAG | ACGTTGCAAC | AGGGGGCGCT | 300 |
| AAACTTGCAG | CAATCCCTAA | CCCCGCCGTT | ATTGAAACGC | TTGAAGCGCG | GGGCGAATCC | 360 |
| ATCATTAAGA | AAGGCGGCAA | GGCGTATCTG | AAAGCCCGCC | AGCAAATAAA | CCAGCGCGGG | 420 |
| CAAATTGTAA | ACCCCTTTAC | GGTTCGCGTA | ACCAAACGCG | GCGAAGTGGT | GCGCCGCTAC | 480 |
| CGCAAGACTA | CCCCG | | | | | 495 |

( 2 ) INFORMATION FOR SEQ ID NO: 9:

( i ) SEQUENCE CHARACTERISTICS:
   ( A ) LENGTH: 504 base pairs
   ( B ) TYPE: nucleic acid
   ( C ) STRANDEDNESS: double
   ( D ) TOPOLOGY: linear ( x i ) SEQUENCE DESCRIPTION: SEQ ID NO: 9:

| | | | | | | |
|---|---|---|---|---|---|---|
| GGGGATACGT | AAAACACTAA | GCCCCTTTTC | ATCATTTCAT | TTGTAAGCGC | GTTTAAAATC | 60 |
| ATGGTAAAAT | AACCACTACC | CCAAATTGCG | CCCCTGCAAT | TTGCTGACGG | TTTAACGGAA | 120 |
| GGCGGAAACA | TGGCGAAGAA | AAAACCAGTA | GAAAAAAATG | GGCTTGTTTA | TAAAGAGTTT | 180 |
| CAAAAACAAG | TTTCAAATTT | GAAGAAAGCC | GGACTAATCC | CTAAAACCCT | TGACGTGCGA | 240 |
| AAAGTCAAGC | CAACAAAACA | CTATAAAGGA | TTGGTAAGCA | AATATAAAGA | CGTTGCAACA | 300 |
| GGGGGCGCTA | AACTTGCAGC | AATCCCTAAC | CCCGCCGTTA | TTGAAACGCT | TGAAGCGCGG | 360 |
| GGCGAATCCA | TCATTAAGAA | AGGCGGCAAG | GCGTATCTGA | AAGCCCGCCA | GCAAATAAAC | 420 |
| CAGCGCGGGC | AAATTGTAAA | CCCCTTTACG | GTTCGCGTAA | CCAAACGCGG | CGAAGTGGTG | 480 |
| CGCCGCTACC | GCAAGACTAC | CCCG | | | | 504 |

( 2 ) INFORMATION FOR SEQ ID NO: 10:

( i ) SEQUENCE CHARACTERISTICS:
   ( A ) LENGTH: 509 base pairs
   ( B ) TYPE: nucleic acid
   ( C ) STRANDEDNESS: double
   ( D ) TOPOLOGY: linear ( x i ) SEQUENCE DESCRIPTION: SEQ ID NO: 10:

| | | | | | | |
|---|---|---|---|---|---|---|
| GGGGATACGT | GCCCCAAAAC | ACTAAGCCCC | TTTTCATCAT | TTCATTTGTA | AGCGCGTTTA | 60 |
| AAATCATGGT | AAAATAACCA | CTACCCCAAA | TTGCGCCCCT | GCAATTTGCT | GACGGTTTAA | 120 |
| CGGAAGGCGG | AAACATGGCG | AAGAAAAAAC | CAGTAGAAAA | AAATGGGCTT | GTTTATAAAG | 180 |
| AGTTTCAAAA | ACAAGTTTCA | AATTTGAAGA | AAGCCGGACT | AATCCCTAAA | ACCCTTGACG | 240 |
| TGCGAAAAGT | CAAGCCAACA | AAACACTATA | AAGGATTGGT | AAGCAAATAT | AAAGACGTTG | 300 |
| CAACAGGGGG | CGCTAAACTT | GCAGCAATCC | CTAACCCCGC | CGTTATTGAA | ACGCTTGAAG | 360 |
| CGCGGGGCGA | ATCCATCATT | AAGAAAGGCG | GCAAGGCGTA | TCTGAAAGCC | CGCCAGCAAA | 420 |
| TAAACCAGCG | CGGGCAAATT | GTAAACCCCT | TTACGGTTCG | CGTAACCAAA | CGCGGCGAAG | 480 |
| TGGTGCGCCG | CTACCGCAAG | ACTACCCCG | | | | 509 |

( 2 ) INFORMATION FOR SEQ ID NO: 11:

( i ) SEQUENCE CHARACTERISTICS:
        ( A ) LENGTH: 515 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 11:

```
GGGGATACGT GCCCCTCCCC CAAAACACTA AGCCCCTTTT CATCATTTCA TTTGTAAGCG   60
CGTTTAAAAT CATGGTAAAA TAACCACTAC CCCAAATTGC GCCCCTGCAA TTTGCTGACG  120
GTTTAACGGA AGGCGGAAAC ATGGCGAAGA AAAAACCAGT AGAAAAAAAT GGGCTTGTTT  180
ATAAAGAGTT TCAAAACAA GTTTCAAATT TGAAGAAAGC CGGACTAATC CCTAAAACCC   240
TTGACGTGCG AAAAGTCAAG CCAACAAAAC ACTATAAAGG ATTGGTAAGC AAATATAAAG  300
ACGTTGCAAC AGGGGGCGCT AAACTTGCAG CAATCCCTAA CCCCGCCGTT ATTGAAACGC  360
TTGAAGCGCG GGGCGAATCC ATCATTAAGA AAGGCGGCAA GGCGTATCTG AAAGCCCGCC  420
AGCAAATAAA CCAGCGCGGG CAAATTGTAA ACCCCTTTAC GGTTCGCGTA ACCAAACGCG  480
GCGAAGTGGT GCGCCGCTAC CGCAAGACTA CCCCG                            515
```

( 2 ) INFORMATION FOR SEQ ID NO: 12:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

```
ACGTATCCCC                                                         10
```

( 2 ) INFORMATION FOR SEQ ID NO: 13:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 13:

```
CGGGATACGT GCCCCTCC                                                18
```

( 2 ) INFORMATION FOR SEQ ID NO: 14:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 14:

```
GCGGATACGT GCCCCTCC                                                18
```

( 2 ) INFORMATION FOR SEQ ID NO: 15:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 15:

```
GGCGATACGT GCCCCTCC                                                18
```

( 2 ) INFORMATION FOR SEQ ID NO: 16:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 16:

GGGAATACGT GCCCCTCC                                                                                    18

( 2 ) INFORMATION FOR SEQ ID NO: 17:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 17:

GGGGTTACGT GCCCCTCC                                                                                    18

( 2 ) INFORMATION FOR SEQ ID NO: 18:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 18:

GGGGATAGGT GCCCCTCC                                                                                    18

( 2 ) INFORMATION FOR SEQ ID NO: 19:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 19:

GGGGATACCT GCCCCTCC                                                                                    18

( 2 ) INFORMATION FOR SEQ ID NO: 20:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 20:

GGGGATACGA GCCCCTCC                                                                                    18

( 2 ) INFORMATION FOR SEQ ID NO: 21:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 21:

GGGGATACGT ACCCCTCC                                                                                    18

( 2 ) INFORMATION FOR SEQ ID NO: 22:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 22:

GGGGATACGT GCCCCTCC    18

( 2 ) INFORMATION FOR SEQ ID NO: 23:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 23:

GGGGATACGT GCGCCTCC        18

( 2 ) INFORMATION FOR SEQ ID NO: 24:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 24:

GGGGATACGT GCCGCTCC        18

( 2 ) INFORMATION FOR SEQ ID NO: 25:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 25:

GGGGATACGT GCCCGTCC        18

( 2 ) INFORMATION FOR SEQ ID NO: 26:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 26:

GGGGATACGT GCCCCTCG        18

( 2 ) INFORMATION FOR SEQ ID NO: 27:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 27:

SGASSSSY W S STA W YSSS        18

( 2 ) INFORMATION FOR SEQ ID NO: 28:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 28:

GGTAGGTGGG GAGGGGCACG TATCCCC        27

( 2 ) INFORMATION FOR SEQ ID NO: 29:

( i ) SEQUENCE CHARACTERISTICS:
   ( A ) LENGTH: 26 base pairs
   ( B ) TYPE: nucleic acid
   ( C ) STRANDEDNESS: single
   ( D ) TOPOLOGY: linear ( i i ) MOLECULE TYPE: Other nucleic acid (synthetic DNA)

( x i ) SEQUENCE DESCRIPTION: SEQ ID NO: 29:

GGTAGGTGGG GAGGGGCACG TATCCC  26

( 2 ) INFORMATION FOR SEQ ID NO: 30:

( i ) SEQUENCE CHARACTERISTICS:
      ( A ) LENGTH: 28 base pairs
      ( B ) TYPE: nucleic acid
      ( C ) STRANDEDNESS: single
      ( D ) TOPOLOGY: linear ( i i ) MOLECULE TYPE: Other nucleic acid (synthetic DNA)

( x i ) SEQUENCE DESCRIPTION: SEQ ID NO: 30:

GGTAGGTGGG GAGGGGCACG TATCCCCC  28

( 2 ) INFORMATION FOR SEQ ID NO: 31:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 31:

GGGGCACGTA TCCCC  15

( 2 ) INFORMATION FOR SEQ ID NO: 32:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 32:

GGAGGGGCAC GTATCCCC  18

( 2 ) INFORMATION FOR SEQ ID NO: 33:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 33:

GGGGAGGGGC ACGTATCCCC  20

( 2 ) INFORMATION FOR SEQ ID NO: 34:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 34:

GGAGGGGCAC GTATCCCG  18

( 2 ) INFORMATION FOR SEQ ID NO: 35:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 35:

GGAGGCGCAC GTATCCGC                                                               18

( 2 ) INFORMATION FOR SEQ ID NO: 36:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 36:

GGAGGGGCAC GTATCGCC                                                              18

( 2 ) INFORMATION FOR SEQ ID NO: 37:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 37:

GGAGGGGCAC GTATTCCC                                                             18

( 2 ) INFORMATION FOR SEQ ID NO: 38:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 38:

GGAGGGGCAC GTAACCCC                                                             18

( 2 ) INFORMATION FOR SEQ ID NO: 39:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 39:

GGAGGGGCAC CTATCCCC                                                             18

( 2 ) INFORMATION FOR SEQ ID NO: 40:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 40:

GGAGGGGCAG GTATCCCC                                                             18

( 2 ) INFORMATION FOR SEQ ID NO: 41:

( i ) SEQUENCE CHARACTERISTICS:
        ( A ) LENGTH: 18 base pairs
        ( B ) TYPE: nucleic acid
        ( C ) STRANDEDNESS: single -continued (D) TOPOLOGY: linear (xi) SEQUENCE DESCRIPTION: SEQ ID NO: 41:

GGAGGGGCTC GTATCCCC                                                      18

(2) INFORMATION FOR SEQ ID NO: 42:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 42:

GGAGGGGTAC GTATCCCC                                                      18

(2) INFORMATION FOR SEQ ID NO: 43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 43:

GGAGGGCCAC GTATCCCC                                                      18

(2) INFORMATION FOR SEQ ID NO: 44:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 44:

GGAGGCGCAC GTATCCCC                                                      18

(2) INFORMATION FOR SEQ ID NO: 45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 45:

GGAGCGGCAC GTATCCCC                                                      18

(2) INFORMATION FOR SEQ ID NO: 46:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 46:

GGACGGGCAC GTATCCCC                                                      18

(2) INFORMATION FOR SEQ ID NO: 47:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 47:

CGAGGGGCAC GTATCCCC                                                          18

(2) INFORMATION FOR SEQ ID NO: 48:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (xi) SEQUENCE DESCRIPTION: SEQ ID NO: 48:

GGGGATACGT                                                                   10

(2) INFORMATION FOR SEQ ID NO: 49:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (xi) SEQUENCE DESCRIPTION: SEQ ID NO: 49:

GGGGATACGT GCCCC                                                             15

(2) INFORMATION FOR SEQ ID NO: 50:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (xi) SEQUENCE DESCRIPTION: SEQ ID NO: 50:

GGGGATACGT GCCCCTCC                                                          18

(2) INFORMATION FOR SEQ ID NO: 51:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO: 51:

GGGGATACGT GCCCCTCCCC                                                        20

(2) INFORMATION FOR SEQ ID NO: 52:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (xi) SEQUENCE DESCRIPTION: SEQ ID NO: 52:

GGGGATACGT GCCCCTCCCC ACCTACC                                                27

(2) INFORMATION FOR SEQ ID NO: 53:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 53:

GGGATACGTG CCCCTCCCCA CCTACC                                                 26

(2) INFORMATION FOR SEQ ID NO: 54:

( i ) SEQUENCE CHARACTERISTICS:
 ( A ) LENGTH: 28 base pairs
 ( B ) TYPE: nucleic acid
 ( C ) STRANDEDNESS: double
 ( D ) TOPOLOGY: linear ( x i ) SEQUENCE DESCRIPTION: SEQ ID NO: 54:

GGGGGATACG TGCCCCTCCC CACCTACC    28

( 2 ) INFORMATION FOR SEQ ID NO: 55:

( i ) SEQUENCE CHARACTERISTICS:
 ( A ) LENGTH: 32 base pairs
 ( B ) TYPE: nucleic acid
 ( C ) STRANDEDNESS: single
 ( D ) TOPOLOGY: linear ( i i ) MOLECULE TYPE: Other nucleic acid (synthetic DNA)

( x i ) SEQUENCE DESCRIPTION: SEQ ID NO: 55:

GTCGACCTGC AGGGCCCGGG GATACGTGCC CC    32

( 2 ) INFORMATION FOR SEQ ID NO: 56:

( i ) SEQUENCE CHARACTERISTICS:
 ( A ) LENGTH: 40 base pairs
 ( B ) TYPE: nucleic acid
 ( C ) STRANDEDNESS: single
 ( D ) TOPOLOGY: linear ( i i ) MOLECULE TYPE: Other nucleic acid (synthetic DNA)

( x i ) SEQUENCE DESCRIPTION: SEQ ID NO: 56:

GGGGATACGT GCCCCTCCAT AGGCCCGAAC TATCACAAAC    40

( 2 ) INFORMATION FOR SEQ ID NO: 57:

( i ) SEQUENCE CHARACTERISTICS:
 ( A ) LENGTH: 40 base pairs
 ( B ) TYPE: nucleic acid
 ( C ) STRANDEDNESS: single
 ( D ) TOPOLOGY: linear ( i i ) MOLECULE TYPE: Other nucleic acid (synthetic DNA)

( x i ) SEQUENCE DESCRIPTION: SEQ ID NO: 57:

GGGGATACGT GCCCCTCCCC CAAAACACTA AGCCCCTTTT    40

( 2 ) INFORMATION FOR SEQ ID NO: 58:

( i ) SEQUENCE CHARACTERISTICS:
 ( A ) LENGTH: 15 base pairs
 ( B ) TYPE: nucleic acid
 ( C ) STRANDEDNESS: single
 ( D ) TOPOLOGY: linear ( i i ) MOLECULE TYPE: Other nucleic acid (synthetic DNA)

( x i ) SEQUENCE DESCRIPTION: SEQ ID NO: 58:

AAAACACTAA GCCCC    15

( 2 ) INFORMATION FOR SEQ ID NO: 59:

( i ) SEQUENCE CHARACTERISTICS:
 ( A ) LENGTH: 16 base pairs
 ( B ) TYPE: nucleic acid
 ( C ) STRANDEDNESS: single
 ( D ) TOPOLOGY: linear ( i i ) MOLECULE TYPE: Other nucleic acid (synthetic DNA)

( x i ) SEQUENCE DESCRIPTION: SEQ ID NO: 59:

GAAAACACTA AGCCCC                                                                                                   16

( 2 ) INFORMATION FOR SEQ ID NO: 60:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 60:

GGGGATACGT AAAACACTAA                                                                                               20

( 2 ) INFORMATION FOR SEQ ID NO: 61:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 61:

GGGGATACGT GCCCCAAAAC ACTAAGC                                                                                       27

( 2 ) INFORMATION FOR SEQ ID NO: 62:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 62:

GGGGATACGT GCCCCTCCC                                                                                                19

( 2 ) INFORMATION FOR SEQ ID NO: 63:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 63:

TCGCCATGTT TCCGCCTTC                                                                                                19

( 2 ) INFORMATION FOR SEQ ID NO: 64:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( i v ) ANTI-SENSE: YES ( i x ) FEATURE: 1-15 E primer ( x i ) SEQUENCE DESCRIPTION: SEQ ID NO: 64:

CGGGGTAGTC TTGCG                                                                                                    15

( 2 ) INFORMATION FOR SEQ ID NO: 65:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 65:

CGGGATACGT GCCCCTC 17

( 2 ) INFORMATION FOR SEQ ID NO: 66:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 66:

GCGGATACGT GCCCCTC 17

( 2 ) INFORMATION FOR SEQ ID NO: 67:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 67:

GGCGATACGT GCCCCTCCC 19

( 2 ) INFORMATION FOR SEQ ID NO: 68:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 68:

GCAGGGCCCG GGAATACGTG CCCCTCC 27

( 2 ) INFORMATION FOR SEQ ID NO: 69:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 69:

GCAGGGCCCG GGGTTACGTG CCCCTCC 27

( 2 ) INFORMATION FOR SEQ ID NO: 70:

( i ) SEQUENCE CHARACTERISTICS:
        ( A ) LENGTH: 27 base pairs
        ( B ) TYPE: nucleic acid (C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 70:

GGGCCCGGGG ATAGGTGCCC CTCCCCA 27

(2) INFORMATION FOR SEQ ID NO: 71:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 71:

GGGCCCGGGG ATACCTGCCC CTCCCCA 27

(2) INFORMATION FOR SEQ ID NO: 72:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 72:

GGGCCCGGGG ATACGAGCCC CTCCCCACCT A 31

(2) INFORMATION FOR SEQ ID NO: 73:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 73:

GGGCCCGGGG ATACGTACCC CTCCCCACCT 30

(2) INFORMATION FOR SEQ ID NO: 74:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 74:

GGGCCCGGGG ATACGTGGCC CTCCCCACCT ACC 33

(2) INFORMATION FOR SEQ ID NO: 75:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 75:

```
GGGCCCGGGG ATACGTGCGC CTCCCCACCT                                         30
```

( 2 ) INFORMATION FOR SEQ ID NO: 76:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 76:

```
GGGCCCGGGG ATACGTGCCG CTCCCCACCT A                                       31
```

( 2 ) INFORMATION FOR SEQ ID NO: 77:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 77:

```
GGGCCCGGGG ATACGTGCCC GTCCCCACCT A                                       31
```

( 2 ) INFORMATION FOR SEQ ID NO: 78:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 78:

```
GGGCCCGGGG ATACGTGCCC CTCGCCACCT ACCCG                                   35
```

( 2 ) INFORMATION FOR SEQ ID NO: 79:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 79:

```
AAAAAAAAAA AAAAAAAAA AAAAAAA                                             27
```

( 2 ) INFORMATION FOR SEQ ID NO: 80:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 80:

```
CCCCCCCCCC CCCCCCCCC CCCCCCC                                             27
```

( 2 ) INFORMATION FOR SEQ ID NO: 81:

( i ) SEQUENCE CHARACTERISTICS:
        ( A ) LENGTH: 27 base pairs (B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 81:

GGGGGGGGGG GGGGGGGGG GGGGGGG　　　　　　　　　　　　　　　　　27

(2) INFORMATION FOR SEQ ID NO: 82:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 82:

GGTAGGTGGG GAGGGCACG TATCC　　　　　　　　　　　　　　　　　　25

(2) INFORMATION FOR SEQ ID NO: 83:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 83:

GGTAGGTGGG GAGGGCACG TATC　　　　　　　　　　　　　　　　　　24

(2) INFORMATION FOR SEQ ID NO: 84:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 84:

GGTAGGTGGG GAGGGCACG TAT　　　　　　　　　　　　　　　　　　　23

(2) INFORMATION FOR SEQ ID NO: 85:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 85:

GGTAGGTGGG GAGGGG　　　　　　　　　　　　　　　　　　　　　　16

(2) INFORMATION FOR SEQ ID NO: 86:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: Other nucleic acid (synthetic DNA)

(ix) FEATURE:

-continued (D) OTHER INFORMATION: base pair 10, represented by
        N, is cytidine (xi) SEQUENCE DESCRIPTION: SEQ ID NO: 86:

W SSTA W YSSN                                                                                    10

(2) INFORMATION FOR SEQ ID NO: 87:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 87:

W SSTA W YSSG                                                                                    10

(2) INFORMATION FOR SEQ ID NO: 88:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 88:

W SSTA W YSSC C                                                                                  11

(2) INFORMATION FOR SEQ ID NO: 89:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 89:

W SSTA W YSSG C                                                                                  11

We claim:

1. A DNA replication sequence adapted to couple to the 3' end of a DNA strand wherein said DNA strand is not natively coupled to the DNA replication sequence the DNA replication sequence having a DNA sequence selected from the group consisting of SEQ ID No. 1, SEQ ID No. 86, SEQ ID No. 87, SEQ ID No. 88, and SEQ ID No. 89.

2. A DNA replication sequence adapted to couple to the 5' end of a DNA strand wherein said DNA strand is not natively coupled to the DNA replication sequence the DNA replication sequence having DNA sequence SEQ ID No. 48.

3. A method for DNA replication, the method comprising the steps of:
   (a) providing a DNA template comprising a DNA strand of interest to which is coupled at the 3' end a DNA replication sequence having a DNA sequence selected from the group consisting of SEQ ID No. 1, SEQ ID No. 86, SEQ ID No. 87, SEQ ID No. 88, and SEQ ID No. 89, and wherein the DNA strand of interest is not natively coupled to the replicating DNA sequence;
   (b) adding to the DNA template PRD1 DNA polymerese, PRD1 terminal protein, and excess quantities of dNTPs; and
   (c) incubating the DNA template, polymerase, protein and dNTP mixture under conditions favoring PRD1-catalyzed DNA replication.

4. A method for DNA replication, the method comprising the steps of:
   (a) providing a DNA template comprising a DNA strand of interest to which is coupled at the 5' end a DNA replication sequence having Sequence ID No. 48, and wherein the DNA strand of interest is not natively coupled to the replicating DNA sequence;
   (b) adding to the DNA template PRD1 DNA polymerase PRD1 terminal protein, end excess quantities of dNTPs; and
   (c) incubating the DNA template, polymerase, protein and dNTP mixture under conditions favoring PRD1-catalyzed DNA replication.

* * * * *